(12) United States Patent
Miyahara et al.

(10) Patent No.: US 10,898,426 B2
(45) Date of Patent: Jan. 26, 2021

(54) ALPHA-GEL FORMATION COMPOSITION, EXTERNAL SKIN CARE COMPOSITION USING ALPHA-GEL FORMATION COMPOSITION, AND ALPHA-GEL COMPOSITION USING ALPHA-GEL FORMATION COMPOSITION

(71) Applicant: SHISEIDO COMPANY, LTD., Tokyo (JP)

(72) Inventors: Reiji Miyahara, Yokohama (JP); Takashi Oka, Yokohama (JP); Makoto Uyama, Yokohama (JP); Saori Tanabe, Yokohama (JP); Tetsuro Yonezawa, Yokohama (JP); Miho Yajima, Yokohama (JP); Noriko Ohira, Yokohama (JP); Saori Nishikawa, Yokohama (JP)

(73) Assignee: SHISEIDO COMPANY, LTD., Tokyo (JP)

( * ) Notice: Subject to any disclaimer, the term of this patent is extended or adjusted under 35 U.S.C. 154(b) by 0 days.

(21) Appl. No.: 16/509,901

(22) Filed: Jul. 12, 2019

(65) Prior Publication Data
US 2019/0350833 A1 Nov. 21, 2019

Related U.S. Application Data

(63) Continuation-in-part of application No. 16/073,155, filed as application No. PCT/JP2017/003070 on Jan. 27, 2017, now abandoned.

(30) Foreign Application Priority Data

Jan. 27, 2016 (JP) .................................. 2016-013168

(51) Int. Cl.
*A61K 8/86* (2006.01)
*A61K 8/06* (2006.01)
(Continued)

(52) U.S. Cl.
CPC ................ *A61K 8/86* (2013.01); *A61K 8/064* (2013.01); *A61K 8/19* (2013.01); *A61K 8/345* (2013.01);
(Continued)

(58) Field of Classification Search
CPC . A61K 8/86; A61K 8/347; A61K 8/37; A61K 8/891; A61K 8/418; A61K 8/345;
(Continued)

(56) References Cited

U.S. PATENT DOCUMENTS

| | | | | |
|---|---|---|---|---|
| 6,419,962 | B1* | 7/2002 | Yokoyama | ............... A61K 8/06 424/725 |
| 2007/0166270 | A1 | 7/2007 | Neuss | |
| 2012/0164086 | A1* | 6/2012 | Araki | ................... B01J 13/0065 424/59 |

FOREIGN PATENT DOCUMENTS

| | | |
|---|---|---|
| EP | 2 177 201 | 4/2010 |
| EP | 2 735 309 | 5/2014 |

(Continued)

OTHER PUBLICATIONS

PCT/JP2017/003070, Written Opinion and International Search Report, dated Apr. 4, 2017, 4 pages—English, 7 pages—Japanese.
(Continued)

*Primary Examiner* — Robert A Wax
*Assistant Examiner* — Quanglong N Truong
(74) *Attorney, Agent, or Firm* — Andrew F. Young, Esq.; Nolte Lackenbach Siegel (57) ABSTRACT

The present invention addresses the problem of providing an α-gel formation composition and an α-gel composition that uses the α-gel formation composition, wherein said compositions are highly stable, do not deposit crystals, become more viscous over time, and, when used in a preparations for external use, are refreshing during application and have high
(Continued)

skin-moisturizing action after application. A gel composition that includes a polyoxyethylene dialkyl ester and/or a polyoxyethylene dialkyl ether, a polyoxyethylene alkyl ester and/or a polyoxyethylene alkyl ether, and, preferably, a polyoxyethylene sterol ether and water.

7 Claims, 4 Drawing Sheets

(51) Int. Cl.
    A61Q 19/00    (2006.01)
    A61K 8/19     (2006.01)
    A61K 8/81     (2006.01)
    A61K 8/92     (2006.01)
    A61K 8/34     (2006.01)
    A61K 8/41     (2006.01)
    A61K 8/891    (2006.01)
    A61K 8/37     (2006.01)

(52) U.S. Cl.
    CPC ............. *A61K 8/347* (2013.01); *A61K 8/37* (2013.01); *A61K 8/418* (2013.01); *A61K 8/8147* (2013.01); *A61K 8/891* (2013.01); *A61K 8/92* (2013.01); *A61Q 19/00* (2013.01)

(58) Field of Classification Search
    CPC .......... A61K 8/92; A61K 8/8147; A61K 8/19; A61K 8/064; A61K 8/922; A61K 8/342; A61K 8/39; A61Q 19/00; A61Q 5/02; A61Q 19/10
    See application file for complete search history.

(56) References Cited

FOREIGN PATENT DOCUMENTS

| JP | 2000-1423 | 1/2000 |
|----|-----------|--------|
| JP | 2002-29915 | 1/2002 |
| JP | 2006-111620 | 4/2006 |
| JP | 2009-51810 | 3/2009 |
| JP | 2009-57515 | 3/2009 |
| JP | 2010-120857 | 6/2010 |
| JP | 2011-32265 | 2/2011 |
| WO | WO 91/04009 | 4/1991 |
| WO | WO 2010/090219 | 8/2010 |

OTHER PUBLICATIONS

PCT/JP2017/000243 Written Opinion and International Search Report, dated Apr. 4, 2017, 8 pages—English, 7 pages—Japanese.

"Applications of Phospholipid to Cosmetics", by Konno, Skin-care Product Development Laboratories, Research Laboratories, KOSE Corporation, J. Soe, Cosmet. Chem. Jpn., vol. 45, No. 2, 2011, 1 page—English, 8 pages—Japanese (pp. 83-90).

The viscosity stability of O/W emulsion containing α-gel through an ionic-compex system, by Uyama, Ikuta, Teshigawara, Watnabe, Miyahara, Journal of Oleo-Science, Copyright 2013 by Japan Oil Chemists' Society, J. Oleo Sci. 62 (1) Sep. 16, 2013, , http://www.jstage.jst.go.jp/browse/jos/, pp. 9-16.

α-Gel Prepared in Sodium Methyl Stearoyl Taurate/Behenyl Alcohol/Water system—Characterization of Structural Changes with Water Concentration, by Watanabe, Inoue, Teshigawara and Kimura, Jouranal of Oleo Science, Copyrigh 2012 by Japan Oil Chemists' Society, J. Oleo Sci. 61 (1) 29-334 (2012), http://www.jstage.jst.go.jp/browse/jos/, pp. 29-34.

A Study on skin hydration with cream, by Nishiyama, Komatsu, Tanaka, Shiseido Laboratories, J. Soc. Cosmet. Chem. Japan, , vol. 16 No. 2 1983, pp. 136-143, English abstract and partial translation throughout.

Formation of Pseudo-Intercellular Lipids Membrance on the Skin Surface by the Alpha-Gel Holding a Large Amount o fWater, by Orita, Uchiyama, Hanamoto, Yamashita, Naitou, Takeuchi, Katayama, Tanabe, Fukuda, Okada, Journal of Japan Cosmetic Engineers, vol. 46, No. 1 2012, pp. 25-32, English abstract and partial translation throughout.

EP 17744447.8, Extended European Search Report dated Jul. 3, 2019, 8 pages—English.

\* cited by examiner

SAXS

FIG. 5B

WAXS

FIG. 6A

Example

FIG. 6B

Comparative Example

FIG. 7A

SAXS

FIG. 7B

WAXS

FIG. 8

ALPHA-GEL FORMATION COMPOSITION, EXTERNAL SKIN CARE COMPOSITION USING ALPHA-GEL FORMATION COMPOSITION, AND ALPHA-GEL COMPOSITION USING ALPHA-GEL FORMATION COMPOSITION

CROSS REFERENCE TO RELATED APPLICATIONS

This application relates to and is a continuation-in-part of U.S. Ser. No. 16/073,115 filed Jul. 26, 2018, the entire contents of which are incorporated herein by reference, which in turn claims the priority as a § 371 national phase of Ser. No.:PCT/JP2017/003070 filed Jan. 27, 2017, the entire contents of which are also incorporated herein by reference which in turn claims priority from Japanese Patent Application No. 2016-013168 filed on Jan. 27, 2016, which is further incorporated herein by reference.

FIELD OF THE INVENTION

The present invention relates to an α-gel forming composition, and an external skin care composition and an α-gel composition using the same, particularly to an α-gel composition substantially (practically) formed only by polyoxyethylene surfactants.

BACKGROUND OF THE INVENTION

α-Gel-containing external skin care preparations, which use α-gel formed by a higher aliphatic alcohol or a higher fatty acid and a hydrophilic surfactant, have been long used for the purpose of maintaining the emulsion stability of external skin care preparations such as cosmetics, quasi-drugs, and pharmaceutical products. Such α-gel has a high viscosity and stabilizes an external skin care preparation but has problems of causing a slimy feel during application and easily depositing crystals of a higher alcohol or a higher fatty acid over time in terms of stability (e.g., see Non-Patent Literature 1).

Additionally, the increase in the viscosity over time commonly occurs and accordingly use of a double-chain cationic surfactant as a viscosity increase inhibitor has been investigated but sufficiently good stability has not yet been achieved (e.g., see Non-Patent Literature 2).

Further, oil components and moisturizers have been blended into external skin care preparations such as cosmetics, quasi-drugs, and pharmaceutical products, for the purpose of preventing rough skin caused by the dry outdoor air. These oil components and moisturizers play a role of sebum which is lost when washed and impart to external skin care preparations with a function as an emollient agent to keep the skin soft and a moisturizing function replacing NMF (natural moisturizing factor). However, these oil components and moisturizers have a drawback of easily causing oiliness and stickiness when blended in a large amount. Particularly, when the α-gel formed by higher aliphatic alcohols or higher fatty acids and a hydrophilic surfactant was blended together for the purpose of maintaining the emulsion stability, a large amount of an aqueous phase is oriented between lamellar layers of the α-gel formed in water (e.g., see Reference Literature 3) and thus the evaporation does not easily occur, making the stickiness during application not disappear easily.

Furthermore, a water-in-oil (W/O) type external skin care preparation provides a high skin protection effect due to the occlusion effect of the oil component (e.g., see Reference Literature 4), however, the α-gel composition has never been blended into water-in-oil (W/O) type external skin care preparations so far because it is basically formed in an aqueous phase.

RELATED PRIOR ART DOCUMENTS

Non-Patent Literature

Non-patent Literature 1: Kei Watanabe et al., J. Oleo Sci., 61, 29-34 (2012)
Non-patent Literature 2: Makoto Uyama et al., J. Oleo Sci., 62, 9-16 (2013)
Non-patent Literature 3: Masanori Oda, Journal of Japan Cosmetic Engineers 46(1), 25-32 (2012)
Non-patent Literature 4: Nishiyama et al., J. Soc. Cosmet. Japan, 16 (2), 136-143 (1983)

DISCLOSURE OF THE INVENTION

Problem to be Solved by the Invention

The present invention was made in view of the prior art, and an object thereof is to provide an α-gel forming composition, and a composition for external skin care use using the same and an α-gel composition using the same which are refreshing during application, have a high skin-moisturizing effect after application, and have a high-stability with no crystal deposition or viscosity increase over time.

Another object is to provide a water-in-oil (W/O) external skin care preparation and an oil-in-water (O/W) external skin care preparation formulating the α-gel forming composition, which are not sticky but refreshing the skin during application even when a large amount of oil components and moisturizers are present and provide a high-emollient effect and a moisturizing effect on the skin once an applied coat is dried.

Means to Solve the Problem

The present inventors conducted extensive studies to solve the above objects and as a result, found that a composition for external skin care use and an α-gel composition using a totally novel α-gel forming composition consisting only of polyoxyethylene surfactants without containing higher alcohols and higher fatty acids have a high skin moisturizing effect and do not have a problem of the over-time stability such as crystal deposition and a viscosity increase over time, whereby the present invention was accomplished.

More specifically, the α-gel forming composition of the present invention comprises: polyoxyethylene dialkyl ester and/or polyoxyethylene dialkyl ether represented by the following formula (I), polyoxyethylene alkyl ester and/or polyoxyethylene alkyl ether represented by the following formula (II), and polyoxyethylene sterol ether represented by the following formula (III):

wherein in the formula (I), R1 and R2 each represent a straight-chain aliphatic acid residue or a straight-chain aliphatic alcohol residue having 16 to 24 carbon atoms, and n represents an integer of 4 to 15, and in the formula (II), R represents a straight-chain aliphatic acid residue or a straight-chain aliphatic alcohol residue having 16 to 24 carbon atoms, and n represents an integer of 8 to 30.

(III)

wherein in the formula (III), R3 represents a cholesterol and/or phytosterol residue, and n represents an integer of 5 to 30.

In the α-gel forming composition, polyoxyethylene dialkyl ester and/or polyoxyethylene dialkyl ether is preferably 15 to 50% by mass, polyoxyethylene alkyl ester and/or polyoxyethylene alkyl ether is preferably 5 to 80% by mass, and polyoxyethylene sterol ether is preferably 80% by mass or less, based on the total amount of the polyoxyethylene surfactants.

The α-gel forming composition comprises water.

The water content in the above forming composition α-gel is preferably 10 to 55% by mass in the α-gel forming composition.

The external skin care composition, according to the present invention, comprises the α-gel forming composition.

The water-in-oil external skin care composition according to the present invention comprises the external skin care composition.

In the water-in-oil external skin care composition preferably further comprises an aliphatic alcohol and/or a fatty acid.

The oil-in-water composition for external skin care use according to the present invention comprises the composition for external skin care use.

The α-gel composition according to the present invention comprises:
polyoxyethylene dialkyl ester and/or polyoxyethylene dialkyl ether represented by the following formula (I),
polyoxyethylene alkyl ester and/or polyoxyethylene alkyl ether represented by the following formula (II), and
polyoxyethylene sterol ether represented by the following formula (III):

(I)

wherein in the formula (I), R1 and R2 each represent a straight-chain aliphatic acid residue or a straight-chain aliphatic alcohol residue having 16 to 24 carbon atoms, and n represents an integer of 4 to 15, (II)

wherein in the formula (II), R represents a straight-chain aliphatic acid residue or a straight-chain aliphatic alcohol residue having 16 to 24 carbon atoms, and n represents an integer of 8 to 30, (III)

wherein in the formula (III), R3 represents a cholesterol and/or phytosterol residue, and n represents an integer of 5 to 30.

Effect of the Invention

The α-gel forming composition, and the α-gel composition using the same according to the present invention do not have a problem of the stability such as crystal deposition and a viscosity increase over time. And yet, the base of the composition is drying up during application and the water content is lesser to form the α-gel formed by polyoxyethylene surfactant having a similar structure, whereby these compositions are refreshing the skin during application and have a good skin moisturizing effect after application.

Additionally, the water-in-oil (W/O) external skin care preparation to which the α-gel forming composition has been blended is separated to a hydrophobic amphiphile component and a hydrophilic amphiphile component in a preparation having a high water content, wherein the hydrophobic amphiphile component is partitioned to an oil phase and the hydrophilic amphiphile component is partitioned to an aqueous phase respectively, and does not contribute to a viscosity increase as the conventional α-gels in which all components are in the aqueous phase. Consequently, the same amphiphile component can be prepared into an oil-in-water (O/W) type emulsification and a water-in-oil (W/O) type emulsification.

The hydrophobic amphiphile component and the hydrophilic amphiphile component become a single phase as water evaporates during application to finally form the α-gel. Thus, the preparation does not take in the aqueous component between the layers enabling a quick coat formation, thus leading to a refreshing feel when used.

BEST MODE FOR CARRYING OUT THE INVENTION

Hereinafter, the constitution according to the present invention is described in detail.

The α-gel forming composition of the present invention does not form an α-gel phase in a region having a high-water-content, but instead, forms a single α-gel phase in a region having a low-water-content.

The polyoxyethylene dialkyl ester and/or ether of (I) used in the present invention preferably has a straight-chain aliphatic acid residue or a straight-chain aliphatic alcohol residue having 16 to 24 carbon atoms, and a polyoxyethylene chain is preferably 4 to 15 mol.

Examples of the commercial product include polyoxyethylene (4 mol) distearate (e.g., manufactured by Nihon Emulsion Co., Ltd., Emalex 200DIS), polyoxyethylene (6 mol) distearate (e.g., manufactured by Nihon Emulsion Co., Ltd., Emalex 300DIS), polyoxyethylene (8 mol) distearate (e.g., manufactured by Nihon Emulsion Co., Ltd., Emalex 400DIS), polyoxyethylene (12 mol) distearate (e.g., manufactured by Nihon Emulsion Co., Ltd., Emalex 600DIS), steareth-4 stearate (e.g., manufactured by Nihon Emulsion Co., Ltd., Emalex SWS-4), steareth-6 stearate (e.g., manufactured by Nihon Emulsion Co., Ltd., Emalex SWS-6), steareth-9 stearate (e.g., manufactured by Nihon Emulsion Co., Ltd., Emalex SWS-9), and polyoxyethylene (8 mol) dibehenyl ether. The binding form of the polyoxyethylene chain and the alkyl group may contain ester, ether, or both of them.

The polyoxyethylene alkyl ester and/or polyoxyethylene alkyl ether of (II) used in the present invention preferably has a straight-chain aliphatic acid residue or a straight-chain aliphatic alcohol residue having 16 to 24 carbon atoms, and a polyoxyethylene chain is preferably 8 to 30 mol.

Examples of the commercial product include polyoxyethylene (5 mol) behenyl ether (e.g., manufactured by Nikko Chemicals, Co., Ltd., Nikkol BB-5), polyoxyethylene (10 mol) behenyl ether (e.g., manufactured by Nikko Chemicals, Co., Ltd., Nikkol BB-10), polyoxyethylene (20 mol) behenyl ether (e.g., manufactured by Nikko Chemicals, Co., Ltd., Nikkol BB-20), polyoxyethylene (10 mol) stearyl ether (e.g., manufactured by Nihon Emulsion Co., Ltd., Emalex 610), and polyoxyethylene (7 mol) cetyl ether (e.g., manufactured by Nihon Emulsion Co., Ltd., Emalex 107).

The polyoxyethylene sterol ether of (III) used in the present invention preferably has, as the hydrophobic group, phytosterol, cholesterol, or ergosterol, and a polyoxyethylene chain is preferably 5 to 30 mol.

Examples of the commercial product include polyoxyethylene (5 mol) phytosterol (e.g., manufactured by Nikko Chemicals, Co., Ltd., Nikkol BPS-5), polyoxyethylene (10 mol) phytosterol (e.g., manufactured by Nikko Chemicals, Co., Ltd., Nikkol BPS-10), polyoxyethylene (20 mol) phytosterol (e.g., manufactured by Nikko Chemicals, Co., Ltd., Nikkol BPS-20), polyoxyethylene (30 mol) phytosterol (e.g., manufactured by Nikko Chemicals, Co., Ltd., Nikkol BPS-30), and polyoxyethylene (10 mol) cholesterol (e.g., manufactured by Nihon Emulsion Co., Ltd., Emalex CS-10).

(α-Gel Phase)

The α-gel is an aggregate formed by a higher aliphatic alcohol and a hydrophilic surfactant in water, and means α-gel taking the α-structure (by Shoji Fukushima, "sechiru arukoru no butsuri kagaku" ("physical chemistry of cetyl alcohol" in English"), published by Fragrance Journal).

(Phase Behavior by Changes in Amount of Water)

The (I) to (III) components were then selected to confirm the phase behavior by changes in the amount of water. Polyoxyethylene (6 mol) distearate (manufactured by Nihon Emulsion Co., Ltd., Emalex 300DIS) was selected as (I) polyoxyethylene dialkyl ester and/or ether.

Further, polyoxyethylene (10 mol) behenyl ether (manufactured by Nikko Chemicals, Co., Ltd., Nikko BB-10) was selected as (II) polyoxyethylene alkyl ester and/or polyoxyethylene alkyl ether.

Furthermore, (10 mol) phytosterol (manufactured by Nikko Chemicals, Co., Ltd., Nikkol BPS-10) was selected as (III) polyoxyethylene sterol ether polyoxyethylene.

Figure 1:
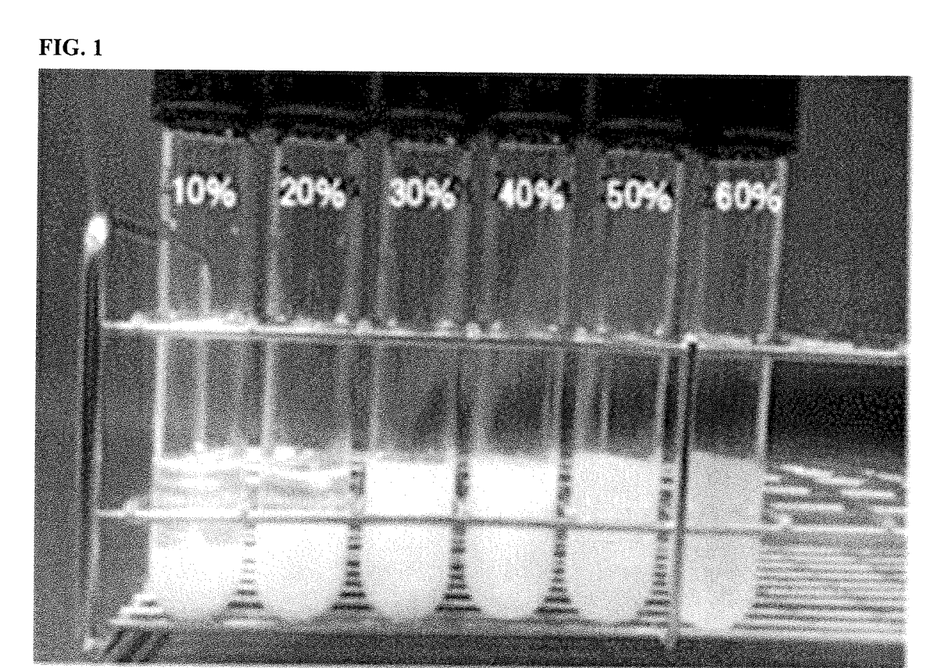
FIG. 1 is a photograph of a sample prepared in (I) component:(II) component:(III) component=1.5:6:2.5 in an active component concentration of 10 to 60% by mass.

When the selected components (I) to (III) are mixed in the ratio of (I):(II):(III)=1.5:6:2.5, the phase state changes to the α-gel phase along with decreasing of the water content and relatively increasing of the concentration of the active components (FIG. 1).

For example, when the concentration of such active components is 10 to 20% by mass, the α-gel phase is not formed.

Figure 2:
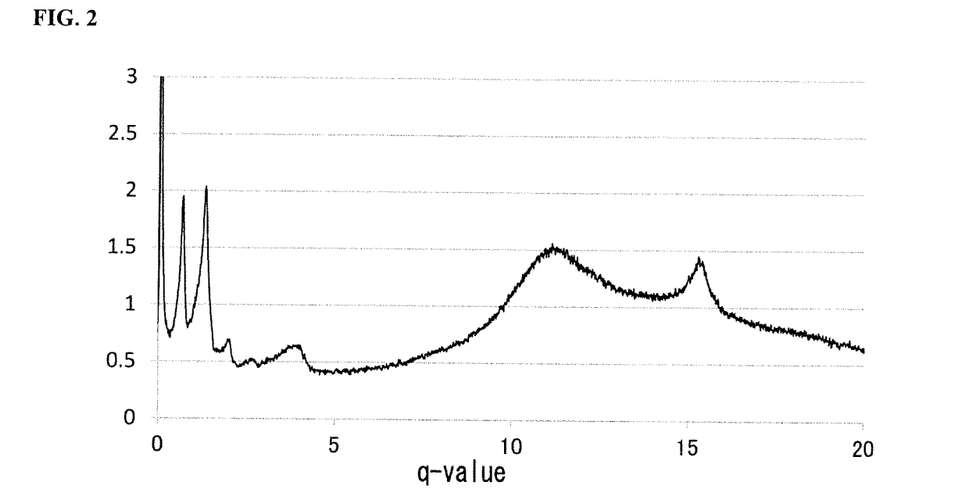
FIG. 2 is an X-ray scattering spectrum of the α-gel according to the present invention.

And when the concentration of the active component is 60% by mass, (I) component, (II) component, and (III) component form α-phase. The α-phase was confirmed by the appearance of scattering peaks suggesting the α-gel (FIG. 2).

Thus, the α-gel phase is not formed due to a high-water-content in a product and during storage over time.

However, when the base components are drying upon and after application and when water is lower, (I) component, (II) component, and (III) component form the α-gel.

Additionally, in the present invention, a plurality of surfactants can be added to the essential components as needed for the purpose of adjusting the usability. Further, the α-gel of the present invention does not form a mixed micelle of the hydrophilic part and the hydrophobic part in the formulation having a lot of water, and thus the substantially same amphiphile component can be prepared into an O/W emulsification with the hydrophilic part, in addition to the W/0 emulsification.

Further, in the external skin care preparation composition, any amounts of the α-gel forming composition, and the α-gel composition using the same can be blended, but generally the total of each nonionic surfactant in the external skin care preparation is preferably 0.1% to 20%.

(Three-Component System Phase Equilibrium Diagram)

Further, the α-gel forming composition according to the present invention can be obtained by further adding (III) polyoxyethylene sterol ether to (I) polyoxyethylene dialkyl ester and/or ether and (II) polyoxyethylene alkyl ester and/or ether, subsequently melting at 70 to 80° C., adding a proportion of 40 to 90% by weight of ion exchange water at 70 to 80° C., stirring and subsequently cooling.

As a specific example of the α-gel composition, polyoxyethylene (6 mol) distearate (manufactured by Nihon Emulsion Co., Ltd., Emalex 300DIS) was selected as (I) component. Further, polyoxyethylene (10 mol) behenyl ether (manufactured by Nikko Chemicals, Co., Ltd., Nikkol BB-10) was selected as (II) component. Additionally, polyoxyethylene (10 mol) phytosterol (manufactured by Nikko Chemicals, Co., Ltd., Nikkol BPS-10) was selected as (III) component.

Figure 3:
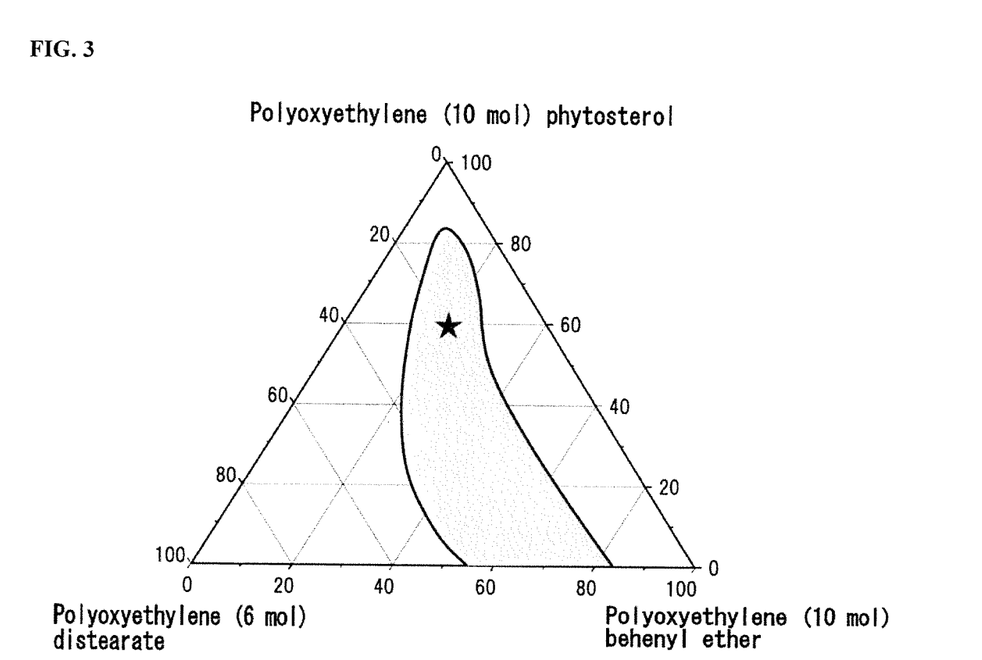
FIG. 3 is a three-component system phase equilibrium diagram of the polyoxyethylene surfactants based α-gel (active surfactant 50% by weight, solvent/water) according to the present invention prepared at 25° C.

A mixture of the selected (I) to (III) components were formed into a single phase at 70 to 80° C. Subsequently, ion exchange water heated to the same temperature was added in a proportion of 50% by weight, and cooled to room temperature (25° C.) to thereby obtain an α-gel composition having a surfactant active component of 50% by weight. A three-component system phase equilibrium diagram is shown in FIG. 3.

Figure 8:
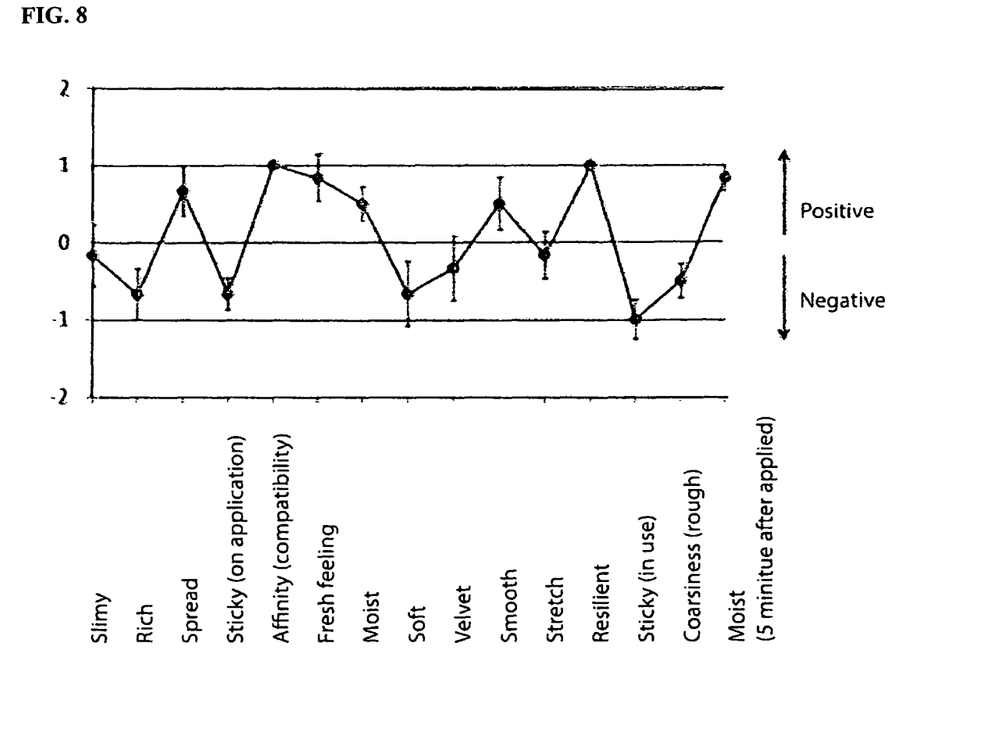
FIG. 8 is use test results by trained panelists on Example 1 according to the present invention compared to Comparative Example 1.

The shaded area in FIG. 8 is a region which had a single melting point peak when measured using a differential calorimeter and obtained scattering peaks (FIG. 2) suggesting the α-gel as a result of X-ray analysis. As is evident in FIG. 3, the α-gel can be obtained only by (I) component and (II) component, but even when (III) component is added, the region of α-gel was also confirmed up to about 80% thereof in the total nonionic surfactants.

In the present invention, nonionic surfactants alone can construct the α-gel forming composition, but a higher aliphatic alcohol having 16 or more carbon atoms can also be added as needed for the purpose of adjusting the usability. Example of the higher aliphatic alcohol having 16 or more carbon atoms include cetyl alcohol, cetostearyl alcohol, stearyl alcohol, behenyl alcohol, and batyl alcohol. Further, the ratio of the polyoxyethylene dialkyl ester and/or ether to the polyoxyethylene alkyl ester and/or polyoxyethylene alkyl ether used in the present invention is preferably (7:3 to 1:9). A ratio outside this range deposits crystals, hence not suitable for the formulation. Additionally, the amount of polyoxyethylene sterol ether to the above mixture is preferably 0 to 80 wt %, and an amount more than this fails to form the α-gel even when a water content reduces during and after application.

The oil component used in the external skin care preparation of the present invention is not particularly limited, and, for example, a liquid oil and fat, a solid oil and fat, a wax, a hydrocarbon oil, a higher fatty acid, a synthetic ester oil, or a silicone oil can be suitably blended, and further some higher alcohols can also be dissolved in these oils and emulsified. The content in the α-gel-containing external skin care preparation of interest is not particularly limited, and 0.05 to 50% by mass is preferable. A content of 0.05% by mass or less results in a poor effect as the external skin care preparation, whereas a content exceeding 50% by mass causes an undesirable feel when used.

Examples of liquid fats include avocado oil, camellia oil, turtle oil, macadamia nut oil, corn oil, mink oil, olive oil, rapeseed oil, egg yolk oil, sesame oil, par chic oil, wheat germ oil, sasanqua oil, castor oil, linseed oil, safflower oil, cotton seed oil, perilla oil, soybean oil, groundnut oil, brown real oil, torreya oil, rice bran oil, Chinese wood oil, jojoba oil, germ oil, and triglycerol.

Examples of solid fats include cacao butter, coconut oil, horse fat, hydrogenated coconut oil, palm oil, beef fat, mutton suet, hydrogenated beef fat, palm kernel oil, lard, beef bones fat, Japan wax kernel oil, hardened oil, hoof oil, Japan wax, and hydrogenated castor oil.

Examples of waxes include beeswax, candelilla wax, cotton wax, carnauba wax, bayberry wax, insect wax, spermaceti, montan wax, bran wax, lanolin, kapok wax, lanolin acetate, liquid lanolin, sugarcane wax, lanolin fatty acid isopropyl, hexyl laurate, reduced lanolin, jojoba wax, hard lanolin, shellac wax, POE lanolin alcohol ether, POE lanolin alcohol acetate, POE cholesterol ether, lanolin fatty acid polyethylene glycol, POE hydrogenated lanolin alcohol ether and cetyl palmitate.

Examples of hydrocarbon oils include liquid paraffin, ozocerite, squalene, pristane, paraffin, ceresin, squalane, vaseline, and microcrystalline wax.

Examples of the higher fatty acid include lauric acid, myristic acid, palmitic acid, stearic acid, behenic acid, oleic acid, undecylenic acid, tall oil acid, isostearic acid, linoleic acid, linolenic acid, eicosapentaenoic acid (EPA), docosahexaenoic acid (DHA).

Examples of the synthetic ester oil include cetyl octanoate, myristyl myristate, glyceryl tri-2-ethylhexanoate, pentaerythritol tetra-2-ethylhexanoate, dioctyl succinate, and tripropylene glycol dineopentanoate.

Examples of the silicone oil include chain polysiloxanes (e.g., dimethyl polysiloxane, methylphenyl polysiloxane, and diphenyl polysiloxane); cyclic polysiloxanes (e.g., octamethylcyclotetrasiloxane, decamethylcyclopentasiloxane, and dodecamethylcyclohexasiloxane), silicone resins having a three-dimensional network, silicone rubbers, various modified polysiloxanes (amino-modified polysiloxane, polyether-modified polysiloxane, alkyl-modified polysiloxane, and fluorine-modified polysiloxane), and acrylic silicones.

The α-gel-containing external skin care preparation of the present invention can be used, for example, in skin cosmetics, hair cleansers, skin cleansers, and hair styling products applicable to the body such as skins and hair.

The α-gel-containing external skin care preparation of the present invention can further contain, in addition to the essential components described above, components typically used in cosmetics and pharmaceutical products at a content in a range which does not affect the stability. Examples of such a component include powder components, amphoteric surfactants, ionic surfactants, nonionic surfactants, moisturizers, thickeners, coating agent, UV absorbers, sequestering agents, pH adjusters, skin nutrients, vitamins, antioxidants, antioxidant aids, and fragrances.

Examples of powder components include inorganic powder (for example, talc, kaolin, mica, sericite, muscovite, phlogopite, synthetic mica, lepidolite, biotite, vermiculite, magnesium carbonate, calcium carbonate, aluminum silicate, barium silicate, calcium silicate, magnesium silicate, strontium silicate, tungstate, magnesium, silica, zeolite, barium sulfate, calcined calcium sulfate, calcium phosphate, fluorine apatite, hydroxyapatite, ceramic powder, metallic soap (for example, zinc myristate, calcium palimitate, and aluminum stearate), and boron nitride); organic powder (for example, polyamide resin powder (nylon powder), polyethylene powder, polymethylmethacrylate powder, polystyrene powder, styrene-acrylic acid copolymer resin powder, benzoguanamine resin powder, poly(tetrafluroethylene) powder, and cellulose powder); inorganic white family pigment (for example, zinc oxide); inorganic red family pigment (for example, iron titanate); inorganic purple family pigment (for example, mango violet, cobalt violet); inorganic green family pigment (for example, chrome oxide, chrome hydroxide, cobalt titanate); inorganic blue family pigment (for example, ultramarine, iron blue); pearl pigment (for example, titanium oxide coated mica, titanium oxide coated bismuth oxychloride, titanium oxide coated talc, colored titanium oxide coated mica, bismuth oxychloride, argentine); metal powder pigment (for example, aluminum powder, and copper powder); organic pigment such as zirconium, barium, or aluminum lake (for example, organic pigment such as Red No. 201, Red No. 202, Red No. 204, Red No. 205, Red No. 220, Red No. 226, Red No. 228, Red No. 405, Orange No. 203, Orange No. 204, Yellow No. 205, Yellow No. 401, Blue No. 404, or Red No. 3, Red No. 104, Red No. 106, Red No. 227, Red No. 230, Red No. 401, Red No. 505, Orange No. 205, Yellow No. 4, Yellow No. 5, Yellow No. 202, Yellow No. 203, Green No. 3, and Blue No. 1); natural pigment (for example, chlorophyll, and β-carotene).

Examples of ampholytic surfactants include imidazoline base ampholytic surfactant (for example, sodium 2-undecyl-N,N,N-(hydroxyethylcarboxymethyl)-2-imidazoline, 2-cocoyl-2-imidazolinium hydroxide-1-carboxyethyloxy)-2-sodium salt; and betaine base surfactant (for example, 2-heptadecyl-N-carboxymethyl-N-hydroxyethylimidazolinium betaine, lauryldimethyl aminoacetate betaine, alkyl betaine, amidobetaine, and sulfobetaine).

Example of ionic surfactants include N-acyl methyl sodium, N-acyl glutamic acid salt, alkyl sulfate, polyoxyethylene alkyl sulfate, fatty acid soap, alkyl quaternary ammonium salt and di alkyl quaternary ammonium salt Examples of lipophilic nonionic surfactants include sorbitan fatty acid esters (for example, sorbitan monooleate, sorbitan monoisostearate, sorbitan monolaurate, sorbitan monopalmitate, sorbitan monostearate, sorbitan sesquioleate, sorbitan trioleate, diglycerol sorbitan penta-2 ethylhexylate, and diglycerol sorbitan tetra-2 ethylhexylate); glyceryl polyglyceryl fatty acids (for example, glyceryl monocotton oil fatty acid, glyceryl monoerucate, glyceryl sesquioleate, glyceryl monostearate, glyceryl e, glyoleate pyroglutamate, and glyceryl monostearate malate); propylene glycol fatty acid esters (for example, propylene glycol monostearate); hydrogenated castor oil derivative; and glyceryl alkyl ether.

Examples of hydrophilic nonionic surfactants include POE-sorbitan fatty acid esters (for example, POE-sorbitan monooleate, POE-sorbitan monostearate, and POE-sorbitan tetraoleate); POE-sorbit fatty acid esters (for example, POE-sorbit monolaurate, POE-sorbit monooleate, POE-sorbit pentaoleate, and POE-sorbit monostearate), POE-glyceryl fatty acid esters (for example, POE-glyceryl monostearate; POE-glyceryl monoisostearate, and POE-glyceryl triisostearate); POE-fatty acid esters (for example, POE-distearate, POE-monodioleate, and ethyleneglycol distearate); POE-alkyl ethers (for example, POE-lauryl ether, POE-oleyl ether, POE-stearyl ether, POE-behenyl ether, POE-2-octyldodecyl ether, and POE-cholestanol ether); pluronic types (for example, Pluronic), POE/POP-alkyl ethers (for example, POE/POP-cetyl ether, POE/POP-2-decyltetradecyl ether, POE/POP-monobutyl ether, POE/POP-hydrogenated lanoline, and POE/POP glycerin ether); tetra POE/tetra POP-ethylenediamine condensation products (for example, Tetronic); POE-castor oil hydrogenated castor oil derivatives (for example, POE-castor oil, POE-hydrogenated castor oil, POE-hydrogenated castor oil monoisostearate, POE-hydrogenated castor oil triisostearate, POE-hydrogenated castor oil monopyroglutamate monoisostearate diester, and POE-hydrogenated oil maleate); POE-beeswax/lanoline derivatives (for example, POE-sorbitol beeswax); alkanolamides (for example, coconut oil fatty acid diethanolamide, lauric acid monoethanolamide, and fatty acid isopropanolamide); POE-propyleneglycol fatty acid esters; POE-alkyl amines; POE-fatty acid amides; sucrose fatty acid esters; alkylethoxydimethylamine oxide; and trioleyl phosphoric acid.

Examples of natural water-soluble polymers include plant-based polymer (for example, gum Arabic, gum tragacanth, galactan, guar gum, locust bean gum, gum karaya, carrageenan, pectine, agar, quince seed (cydonia oblonga), algae colloid (brown algae extract), starch (rice, corn, potato, and wheat), and glicyrrhizic acid), microorganisms based polymer (for example, xanthan gum, dextran, succinoglycan, and pullulan), animal-based polymer (for example, collagen, casein, and albumin, gelatine).

Examples of semisynthetic water-soluble polymers include starch-based polymer (for example, carboxymethyl starch, and methylhydroxypropyl starch), cellulosic polymer (methylcellulose, ethylcellulose, methylhydroxypropylcellulose, hydroxyethylcellulose, cellulose sodium sulfate, hydroxypropylcellulose, carboxymethylcellulose, sodium calboxymethyl cellulose, micrclrystalline cellulose, and cellulose powder), alginic acid base polymer (for example, sodium alginate, and propylene glycol ester alginate) and sodium pectate.

Examples of synthetic water-soluble polymers include vinyl base polymer (for example, polyvinyl alcohol, polyvinyl methyl ether, polyvinylpyrrolidone, and carboxyvinylpolymer); polyoxyethylene base polymer (for example, polyethylene glycol 20,000, 40,000, and 60,000); Poly (dimethyldiallylammonium halide) type cationic polymer (for example, Merquat100 Merck U.S.A Co. ltd); Copolymerizable type cationic polymers of dimethyldiallylammonium halide and acrylamide (for example Merquat550 Merck U.S.A Co. ltd); acrylic polymer (for example, sodium polyacrylate, polyethylacrylate, and polyacrylamide); polyethyleneimine; cationpolymer and magnesium aluminum silicate.

Examples of ultraviolet light absorbers include benzoic acid family ultraviolet light absorbers (for example, p-aminobenzoic acid (hereinafter abbreviated as PABA), PABA monoglycerine ester, N,N-dipropoxy PABA ethyl ester, N,N-diethoxy PABA ethyl ester, N,N-dimethyl PABA ethyl ester, N,N-dimethyl PABA butyl ester, and N,N-dimethyl PABA ethyl ester); anthranilic acid family ultraviolet light absorbers (for example, homomenthyl N-acetylanthranilate); salicylic acid family ultraviolet light absorbers (for example, amyl salicylate, menthyl salicylate, homomenthyl salicylate, octyl salicylate, phenyl salicylate, benzyl salicylate, and p-isopropanolphenyl salicylate); cinnamic acid family ultraviolet light absorbers (for example, octyl cinnamate, ethyl 4-isopropylcinnamate, methyl 2,5-diisopropylcinnamate, ethyl 2,4-diisopropylcinnamate, methyl 2,4-diisopropylcinnamate, propyl p-methoxycinnamate, isopropyl p-methoxycinnamate, isoamyl p-methoxycinnamate, octyl p-methoxycinnamate (2-ethylhexyl p-methoxycinnamate), 2-ethoxyethyl p-methoxycinnamate, cyclohexyl p-methoxycinnamate, ethyl incyano-yaphenylcinnamate, 2-ethylhexyl, cyano-yaphenylcinnamate, and glyceryl mono-2-ethylhexanoyl-diparamethoxy cinnamate); benzophenone family ultraviolet light absorbers (for example, 2,4-dihydroxybenzophenone, 2,2'-dihydroxy-4-methoxybenzophenone, 2,2'-dihydroxy-4,4'-dimethoxybenzophenone, 2,2',4,4'-tetrahydroxybenzophenone, 2-hydroxy-4-methoxybenzophenone, 2-hydroxy-4-methoxy-4'-methylbenzophenone, 2-hydroxy-4-methoxybenzophenone-5-sulfonate, 4-phenylbenzophenone, 2-ethylhexyl-4'-phenyl-benzophenone-2-carboxylate, 2-hydroxy-4-n-octoxybenzophenone, and 4-hydroxy-3-carboxybenzophenone); 3-(4'-methylbenzyl idene)-d,l-camphor, 3-benzylidene-d,l-camphor; 2-phenyl-5-methylbenzoxazol; 2,2'-hydroxy-5-methylphenylbenzotriazol; 2-(2'-hydroxy-5'-t-octylphenyl) benzotriazol, 2-(2'-hydroxy-5'-methylphenylbenzotriazol; dibenzalazine; dianisoylmethane; 4-methoxy-4'-t-butyldibenzoylmethane; and 5-(3, 3-dimethyl-2-norbornyl idene)-3-pentane-2-one.

Example of sequestering agent include 1-hydroxyethane-1,1-diphosphonic acid, 1-hydroxyethane-1,1-diphosphonic acid tetrasodium salt, edetate disodium, edetate trisodium, edetate tetrasodium, sodium citrate, sodium polyphosphate, sodium metaphosphate, gluconic acid, phosphoric acid, citric acid, ascorbic acid, succinic acid, edetic acid and ethylenediamine hydroxyethyl triacetate trisodium.

Examples of the pH adjuster include buffers such as lactic acid-sodium lactate, citric acid-sodium citrate, and succinic acid-sodium succinate.

Examples of the vitamin include vitamins A, B1, B2, B6, C, E, and derivatives thereof, pantothenic acid and derivatives thereof, and biotin.

Examples of the antioxidant include tocopherols, dibutylhydroxytoluene, butylhydroxyanisol, and gallic acid esters.

Examples of anti-oxidant aids include phosphoric acid, citric acid, ascorbic acid, maleic acid, malonic acid, succinic acid, fumaric acid, cephalin, hexamethaphosphate, phytic acid, and ethylene diamine tetra-acetic acid.

Examples of other blendable components include antiseptic agent (ethylparaben, butylparaben, etc.); lightening agent (for example, placental extract, saxifrage extract, and arbutin); blood circulation promotion agent (for example, nicotine acid, nicotine acid benzyl, tocopherol nicotinate, nicotine acid β-butoxy ester, minoxidil, or their analogs, vitamine E type, γ-oryzanol, alkoxycarbonylpyridine N-oxide, capronium chloride, acetylcholine and their derivatives); various extract (for example, ginger, oat, Japanese coptis, lithospermum, birch, loquat, carrot, aloe, mallow, iris, grape, sponge gourd, lily, saffron, cnidium rhizome, ginger, hypericum, restharrow, garlic, red pepper, citrus unshiu, Japanese angelica, Japanese tree peoney, and seaweed); activator agent (for example, pantothenyl ethyl ether, nicotinamide, biotin, pantothenic acid, royal jelly, and cholesterol derivative); and antiseborrheric agent (for example, pyridoxine, and thianthl).

Further, fragrances, scrubbing agents, and the like can suitably be blended in a range which does not affect the stability.

Example

Hereinafter, the present invention is described in further detail in reference with Examples, but not limited thereto. The content is all shown in % by mass, unless specifically stated otherwise.

First of all, absence of the α-gel of the present invention in a formulation having a high-water-content is described in reference with test results. Assuming the situation where water volatilizes and dries, each of the compositions shown in Table 1 was prepared respectively at 75° C. using a common α-gel consisting of stearoyl N-sodium methyltaurate and behenyl alcohol and a α-gel preparation containing polyoxyethylene (10 mol) phytosterol (tradename: Nikkol BPS-10): polyoxyethylene (6 mol) distearate (tradename: Emalex 300DI-S): polyoxyethylene (10 mol) behenyl ether (tradename: Nikkol BB-10) (6:2:2).

In the compositions of Table 1, compositions in the table entry described as α-gel component are shown in Table 2. Both have the same contents of the total α-gel active component.

TABLE 1

| Component | Content | Content | Content | Content | Content |
|---|---|---|---|---|---|
| α-Gel component | 2.68 parts | ditto* | ditto | ditto | ditto |
| Cetyl isooctanoate | 2 parts | ditto | ditto | ditto | ditto |
| Ion exchange water** | 2 parts | 5 parts | 10 parts | 15 parts | 20 parts |

*Ditto: the same as the left
**The parts of ion exchange water are simulated as drying from right to left.

TABLE 2

| | Content |
|---|---|
| α-Gel forming composition of the present invention | |
| (1) Polyoxyethylene (6 mol) distearate | 0.54 Parts |
| (2) Polyoxyethylene (10 mol) behenyl ether | 0.54 Parts |
| (3) Polyoxyethylene (10 mol) phytosterol | 1.6 Parts |
| Common α-gel | |
| (1) Stearyl alcohol | 0.5 Parts |
| (2) Behenyl alcohol | 1.84 Parts |

Figure 4:
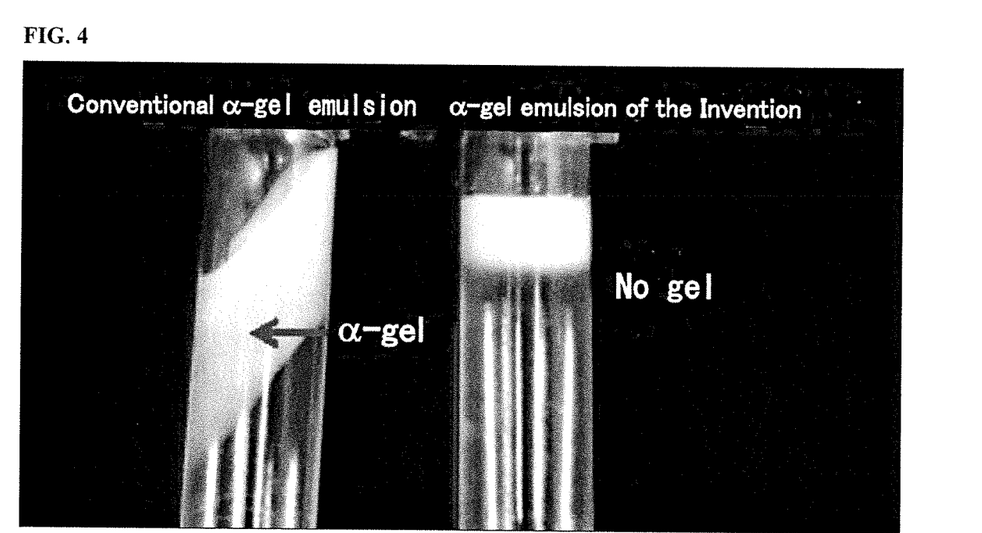
FIG. 4 is observation photographs of a common α-gel containing 20 parts of water and an O/W emulsified formulation of the α-gel forming composition according to the present invention after respectively ultra-centrifuged at 30,000 rpm for 12 hours.
Figure 5A:
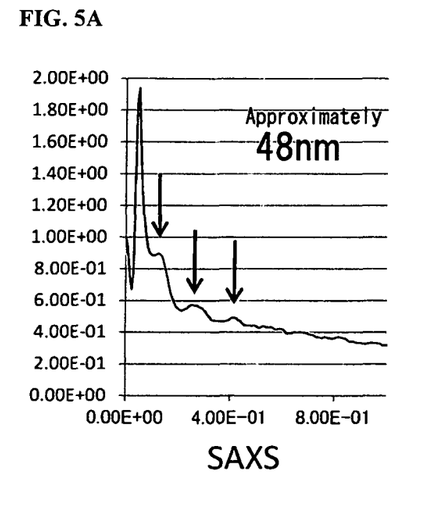
FIG. 5A, 5B are X-ray analysis results of a common α-gel and the α-gel forming composition according to the present invention.
Figure 5B:
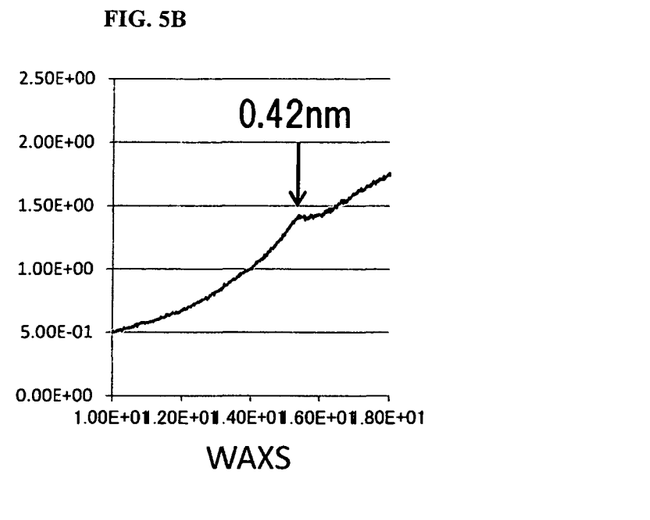

FIG. 4 shows observation photographs of O/W emulsified formulations containing 20 parts of water ultra-centrifuged respectively at 30,000 rpm for 12 hours. As is evident from the photographs, the common α-gel had a separated gel part which was revealed, as shown in FIG. 5A, FIG. 5B, to have a α-gel structure having an interplanar spacing of 48 nm and a sub-lattice spacing of 0.42 nm when X-ray analyzed.

Figure 6A:
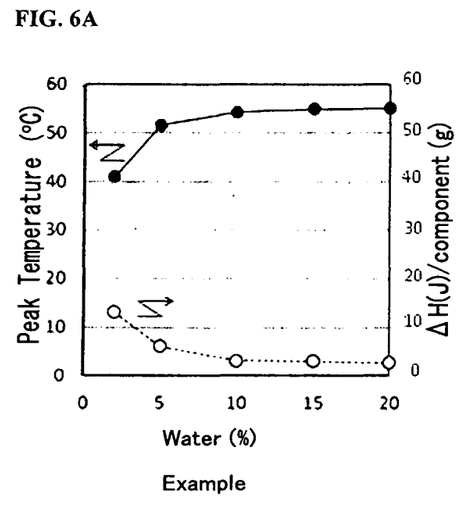
FIG. 6A, 6B are results of differential scanning calorimetry (DSC measurement) of each of the samples having different water contents.
Figure 6B:
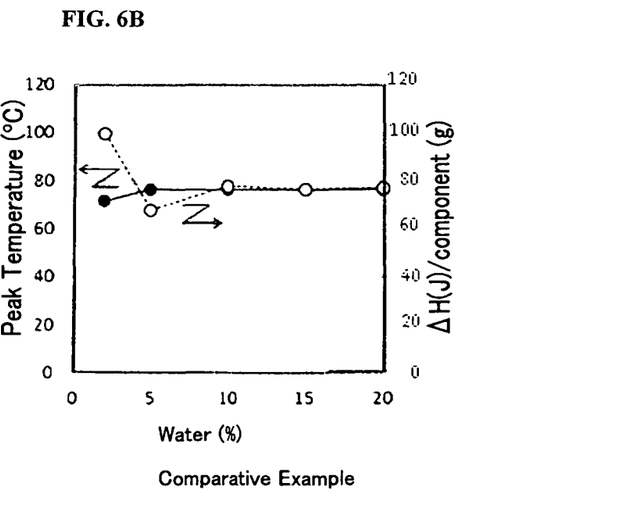
Figure 7A:
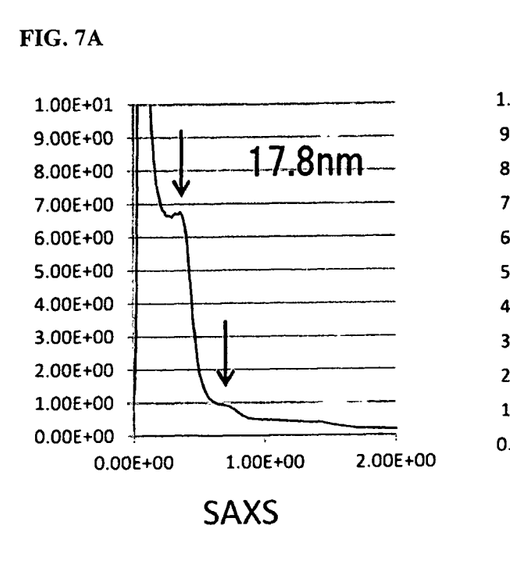
FIG. 7A, 7B are X-ray analysis results of an O/W emulsified formulation of the present α-gel containing only 2 parts of water supposing after dried.
Figure 7B:
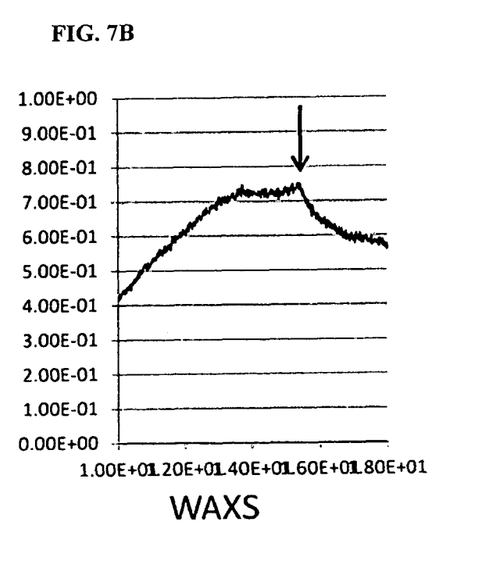

Further, FIGS. 6A and 6B show the results of differential scanning calorimetry (DSC measurement) of each of the samples having different water contents. As is evident in FIG. 6A, FIG. 6B, the α-gel consisting of stearoyl N-sodium methyltaurate and behenyl alcohol, which is the common α-gel, has substantially constant gel melting points and endothermic enthalpy at any water content, but the α-gel forming composition of the present invention had the gel melting points and endothermic enthalpy abruptly changing at a water content of 5 parts or more, and particularly the endothermic enthalpy was revealed to have been almost 0, which coincided with the result of the α-gel inseparable by ultracentrifugation. Further, the X-ray analysis results of the O/W emulsified formulation of the present α-gel containing only 2 parts of water are shown in FIG. 7A, FIG. 7B, but in the state of such a low water content, an interplanar spacing of 17.8 nm was found on the smaller angle side and an α-gel specific sub-lattice spacing of 0.42 nm was found on the wide-angle side.

(Feel of O/W Emulsion Containing the α-Gel Forming Composition when Used)

An O/W emulsion containing the α-gel forming composition of Example 1 containing the polyoxyethylene surfactants based α-gel forming composition according to the present invention (polyoxyethylene (6 mol) distearate, polyoxyethylene (10 mol) behenyl ether, and polyoxyethylene (10 mol) phytosterol) and an emulsion containing the α-gel of Comparative Example 1 using a common higher alcohol based α-gel (behenyl alcohol, stearyl alcohol, and sodium N-stearoyl methyltaurate) were respectively prepared by a routine method. The amounts of components constituting the α-gels were the same, and other components and the amounts of components were identical.

For the use test, proper doses of Example 1 and Comparative Example 1 were respectively applied to half each of the face by 6 trained panelists and feels of use of Example 1 compared to Comparative Example 1 were evaluated on 5 scales for each evaluation entry. Evaluation score 0 was the feel of use equivalent to that of Comparative Example 1.

TABLE 3

| Example 1 | Content % by mass |
|---|---|
| (1) Polyoxyethylene (6 mol) distearate | 0.27 |
| (2) Polyoxyethylene (10 mol) behenyl ether | 0.27 |
| (3) Polyoxyethylene (10 mol) phytosterol | 0.8 |
| (4) Liquid paraffin | 2.3 |
| (5) Dimethylpolysiloxane 6CS | 3.0 |
| (6) Isocetyl octanoate | 0.7 |
| (7) Amino-modified polymer silicone/dimethylpolysiloxane 20CS 10% solution | 0.5 |
| (8) Dynamite glycerin | 3.0 |
| (9) Dipropylene glycol | 7.0 |
| (10) Common alcohol 95% | 5.0 |
| (11) Phenoxy ethanol | 0.5 |
| (12) Carboxy vinyl polymer | 0.015 |
| (13) Caustic potash | 0.63 |
| (14) EDTA2Na•2H2O | 0.03 |
| (15) Ion exchange water | Balance |

TABLE 4

| Comparative Example 1 | Content % by mass |
|---|---|
| (1) Behenyl alcohol | 0.92 |
| (2) Stearyl alcohol | 0.25 |
| (3) Sodium N-stearoyl methyltaurate | 0.17 |
| (4) Liquid paraffin | 2.3 |
| (5) Dimethylpolysiloxane 6CS | 3.0 |
| (6) Cetyl isooctanoate | 0.7 |
| (7) Amino-modified polymer silicone/dimethylpolysiloxane 20CS 10% solution | 0.5 |
| (8) Dynamite glycerin | 3.0 |
| (9) Dipropylene glycol | 7.0 |
| (10) Common alcohol 95% | 5.0 |
| (11) Phenoxy ethanol | 0.5 |
| (12) Carboxy vinyl polymer | 0.015 |
| (13) Caustic potash | 0.63 |
| (14) EDTA2Na•2H2O | 0.03 |
| (15) Ion exchange water | Balance |

(Results)

Results are shown in FIG. 8. As is evident in the figure, the O/W emulsion containing a kind of polyoxyethylene surfactant α-gel forming composition according to the present invention was revealed to have a high moistness feel and a resilient feel after application while easily spreadable and refreshing compared to the emulsion of Comparative Example 1 which used the higher alcohol based α-gel.

(Viscosity Stability Test)

Further, the O/W emulsion containing the α-gel forming composition of Example 1 and the external skin care preparation containing the α-gel of Comparative Example 1 were respectively compared for the viscosity stability.

(Comparison on the Viscosity Stability)

The samples of Example 1 and Comparative Example 1 were stored each at 0 to 50° C., the viscosity over time was retained at 30° C. for 30 minutes or longer, and subsequently measured using a B type viscometer (rotor No. 2 or No. 3, 6 rpm, 1 minute). The measured values are shown in Table 5.

TABLE 5

| Time elapsed, Temperature condition | Example 1 | Comparative Example 1 |
|---|---|---|
| Day 1 | 2530 mPa · s | 7450 mPa · s |
| 1 Month 0° C. | 2450 | 17580 |
| 1 Month 25° C. | 2590 | 20080 |
| 1 Month 37° C. | 2460 | 15430 |
| 1 Month 50° C. | 2380 | 14600 |
| 2 Months 0° C. | 2550 | 25380 |
| 2 Months 25° C. | 2610 | 30250 |
| 2 Months 37° C. | 2540 | 18650 |
| 2 Months 50° C. | 2400 | 17630 |

As is evident in Table 5, the emulsion of Example 1 was revealed to have maintained constant viscosity compared to Comparative Example 1. This is because in Comparative Example 1 the higher aliphatic alcohol, which is the constituting component of the α-gel causing the viscosity, is dissolved in the oil phase and sodium N-stearoyl methyltaurate is dissolved in the aqueous phase wherein the higher aliphatic alcohol present in the oil phase flows out into the aqueous phase and gradually mixes with sodium N-stearoyl methyltaurate to thereby increase the viscosity, whereas the α-gel forming composition of the present invention is constituted with the nonionic surfactants all having similar solubilities.

(Feel of W/O Emulsion Containing the α-Gel Forming Composition when Used)

A W/O cream containing the α-gel forming composition of Example 1 containing polyoxyethylene (6 mol) distearate, polyoxyethylene (10 mol) behenyl ether, polyoxyethylene (10 mol) phytosterol, and polyoxyethylene (10 mol) behenyl ether, and other 3 different kinds of W/O creams were respectively prepared by a routine method.

For the use test, sensory evaluations were carried out when each of the W/O creams was applied by 10 trained panelists and average values obtained by evaluating on 5 scale scores are shown in the table.

| (Criteria for sensory evaluation on sticky feel) | | |
|---|---|---|
| Sticky feel | Very intense | 1 |
| | Intense | 2 |
| | Fair | 3 |
| | Rather weak | 4 |
| | Weak | 5 |
| (Criteria for sensory evaluation on skin compatibility) | | |
| Skin compatibility | Very intense | 1 |
| | Intense | 2 |
| | Fair | 3 |
| | Rather weak | 4 |
| | Weak | 5 |

TABLE 6

| Component | Test sample 1 | Comparative sample 1 | Comparative sample 2 | Comparative sample 3 |
|---|---|---|---|---|
| Polydimethylsiloxane 6CS | 5 | 5 | 5 | 5 |
| Liquid paraffin | 15 | 15 | 15 | 15 |
| Isocetyl octanoate | 5 | 5 | 5 | 5 |
| Purified Vaseline | 10 | 10 | 10 | 10 |
| Microcrystalline wax | 0.5 | 0.5 | 0.5 | 0.5 |
| Quaternium-5 hectorite | 2 | 2 | 2 | 2 |
| Polyoxyethylene (10 mol) phytosterol | 0.6 | — | — | — |

TABLE 6-continued

| Component | Test sample 1 | Comparative sample 1 | Comparative sample 2 | Comparative sample 3 |
|---|---|---|---|---|
| Polyoxyethylene (6 mol) distearate | 0.2 | — | — | — |
| Polyoxyethylene (10 mol) behenyl ether | 0.2 | — | — | — |
| Diglyceryl isostearate | 0.2 | 1.2 | — | — |
| Sorbitan sesquioleate | — | — | 1.2 | — |
| (Diisostearate/polyhydroxystearate/sebacate)polyglyceryl-4 | — | — | — | 1.2 |
| Glycerin | 7 | 7 | 7 | 7 |
| Dipropylene glycol | 3 | 3 | 3 | 3 |
| 1,3-Butandiol | 3 | 3 | 3 | 3 |
| Phenoxy ethanol | 0.5 | 0.5 | 0.5 | 0.5 |
| Ion exchange water | 47.8 | 47.8 | 47.8 | 47.8 |
| Sticky feel | 4.5 | 3.5 | 3.2 | 2.9 |
| Skin compatibility | 4.3 | 3.2 | 2.8 | 3.3 |

As is evident in Table 6, the W/O cream containing the α-gel forming composition of the present invention was revealed to have been sensed having a less sticky feel and quick skin compatibility compared to the W/O creams obtained by other emulsification methods.

(Moisturizing (Occlusion) Effect Test)

Further, the skin moisturizing effects of the W/O creams of Example 1 and Comparative Examples 1 to 3 were evaluated as the occlusion effect. More specifically, each formulation was homogeneously applied to a filter paper in a rate of 5 mg/cm2 and allowed to stand for 1 day. In a thermo-hygrostat (23° C., relative humidity=45%), 5 mL of water was placed in a 25 mL vial, immediately the filter paper was inserted and fixed with the cap of the vial, and an amount of water evaporated was measured successively. The amount of water evaporated per hour (attenuation wt %) was defined as water evaporation rate constant (%/hour). Thus, the smaller a water evaporation rate constant (%/hour) is, the higher the ability to retain water is.

TABLE 7

| Test base | Water evaporation rate constant (%/hour) |
|---|---|
| Ion exchange water (Blank) | 0.143 |
| Example Formulation 1 | 0.019 |
| Comparative Formulation 1 | 0.038 |
| Comparative Formulation 2 | 0.029 |
| Comparative Formulation 3 | 0.033 |

As is evident in Table 7, the W/O cream containing the α-gel forming composition of the present invention (Example Formulation 1) was revealed to have a higher occlusion effect compared to the W/O creams obtained by other emulsification methods (Comparative Examples 1 to 3).

Hereinafter, the present invention is further described in reference with Examples, but is not limited thereto.

TABLE 8

| Example 2 O/W Emulsion | Content % by mass |
|---|---|
| (1) Polyoxyethylene (6 mol) distearate | 0.3 |
| (2) Polyoxyethylene (10 mol) behenyl ether | 0.5 |
| (3) Polyoxyethylene (10 mol) phytosterol | 1.2 |
| (4) Dipropylene glycol | 5.0 |
| (5) Fragrance | 0.1 |
| (6) Pentaerythritol tetra2-ethylhexanoate | 2.0 |
| (7) α-Olefin oligomer | 3.0 |
| (8) Dimethylpolysiloxane *1 | 2.0 |
| (9) Purified vaseline | 1.0 |
| (10) 1,3-Butylene glycol | 2.0 |
| (11) Phenoxyethanol | 0.5 |
| (12) Glycerin | 4.0 |
| (13) Carboxy vinyl polymer | 0.03 |
| (14) Potassium hydroxide | 0.01 |
| (15) Tranexamic acid | 0.1 |
| (16) Citric acid | 0.02 |
| (17) Sodium citrate | 0.08 |
| (18) Ion exchange water | Balance |

*1 Dimethylpolysiloxane (manufactured by Shin-Etsu Chemical Co., Ltd., Silicone KF96-A6T)

(Production Method)

The emulsification was carried out by a routine method to obtain the above emulsion. The obtained emulsion was not slimy but refreshing when used and had good viscosity stability.

TABLE 9

| Example 3 O/W Serum | Content % by mass |
|---|---|
| (1) Sodium N-stearoyl methyltaurate | 0.01 |
| (2) Polyoxyethylene (6 mol) distearate | 0.2 |
| (3) Polyoxyethylene (10 mol) behenyl ether | 0.2 |
| (4) Polyoxyethylene (10 mol) phytosterol | 0.6 |
| (5) Liquid paraffin | 0.78 |
| (6) Methylphenylpolysiloxane *2 | 0.2 |
| (7) Fragrance | 0.02 |
| (8) Polyoxyethylene (14 mol) polyoxypropylene (7 mol) dimethyl ether | 0.5 |
| (9) Glycerin | 3.0 |
| (10) Dipropylene glycol | 5.0 |
| (11) 1,3-Butylene glycol | 3.0 |
| (12) Citric acid | 0.02 |
| (13) Sodium citrate | 0.08 |
| (14) EDTA2Na•2H2O | 0.01 |
| (15) Common alcohol 95% | 5.0 |
| (16) Phenoxyethanol | 0.5 |
| (17) Ion exchange water | Balance |

*2 Methylphenylpolysiloxane (manufactured by Shin-Etsu Chemical Co., Ltd., Silicone KF56)

(Production Method)

The emulsification was carried out by a routine method to obtain the above serum. The obtained serum was not slimy but refreshing when used and had good viscosity stability.

TABLE 10

| Example 4 O/W Emulsion | Content % by mass |
|---|---|
| (1) Polyoxyethylene (8 mol) distearate | 0.5 |
| (2) Polyoxyethylene (10 mol) stearyl ether | 1.0 |
| (3) Polyoxyethylene (10 mol) phytosterol | 5.0 |
| (4) Isopropylene glycol | 4.5 |
| (5) 1,4-Butandiol | 1.5 |
| (6) Fragrance | 0.09 |
| (7) Glyceryl tristearate | 2.5 |
| (8) Squalane | 4.5 |
| (9) Dimethylpolysiloxane *1 | 1.0 |
| (10) Dipropylene glycol | 7.0 |
| (11) Erythritol | 1.3 |

TABLE 10-continued

| Example 4 O/W Emulsion | Content % by mass |
|---|---|
| (12) Dynamite glycerin | 6.0 |
| (13) Phenoxyethanol | 0.3 |
| (14) Xanthan gum | 0.5 |
| (15) Sodium hexametaphosphate | 0.03 |
| (16) Ion exchange water | Balance |

(Production Method)

The emulsification was carried out by a routine method to obtain the above emulsion. The obtained emulsion was not slimy but refreshing when used and had good viscosity stability.

TABLE 11

| Example 5 O/W Sun block cream | Content % by mass |
|---|---|
| (1) Polyoxyethylene (4 mol) distearate | 0.4 |
| (2) Polyoxyethylene (10 mol) cetyl ether | 0.4 |
| (3) Polyoxyethylene (10 mol) cholesterol | 1.5 |
| (4) Dipropylene glycol | 6.0 |
| (5) Fragrance | 0.08 |
| (6) Glyceryl tri2-ethylhexanoate | 2.0 |
| (7) Di-2-ethylhexyl succinate | 3.0 |
| (8) 2-Ethylhexyl p-methoxycinnamate | 5.0 |
| (9) Avobenzone | 3.0 |
| (10) Bis-ethylhexyloxyphenol methoxyphenyl triazine | 1.0 |
| (11) 1,3-Butylene glycol | 5.0 |
| (12) Phenoxyethanol | 0.5 |
| (13) Glycerin | 9.0 |
| (14) EDTA-trisodium salt | 0.1 |
| (15) Erythritol | 0.1 |
| (16) Citric acid | 0.02 |
| (17) Sodium citrate | 0.08 |
| (18) Ion exchange water | Balance |

(Production Method)

The emulsification was carried out by a routine method to obtain the above sun block cream. The obtained sun block cream was not slimy but refreshing when used, and had good viscosity stability.

TABLE 12

| Example 6 O/W Cream | Content % by mass |
|---|---|
| (1) Polyoxyethylene (6 mol) behenic acid | 0.7 |
| (2) Polyoxyethylene (30 mol) behenyl ether | 0.9 |
| (3) Polyoxyethylene (5 mol) phytosterol | 2.0 |
| (4) 1,3-Butylene glycol | 6.5 |
| (5) Ion Exchange water | Balance |
| (6) Fragrance | 0.05 |
| (7) Dimethylpolysiloxane *1 | 7.4 |
| (8) Squalane | 4.0 |
| (9) Behenyl alcohol | 0.6 |
| (10) Purified vaseline | 1.0 |
| (11) Dipropylene glycol | 5.0 |
| (12) Phenoxyethanol | 0.5 |
| (13) Glycerin | 7.0 |
| (14) EDTA-trisodium salt | 0.1 |
| (15) Camomile extract | 0.1 |
| (16) Citric acid | 0.02 |
| (17) Sodium citrate | 0.08 |

(Production Method)

The emulsification was carried out by a routine method to obtain the cream. The obtained cream was not slimy but refreshing when used, and had good viscosity stability.

TABLE 13

| Example 7 W/O Sun block cream | Content % by mass |
|---|---|
| (1) Polyoxyethylene (4 mol) distearate | 0.4 |
| (2) Polyoxyethylene (10 mol) cetyl ether | 0.4 |
| (3) Polyoxyethylene (10 mol) cholesterol | 1.5 |
| (4) Dipropylene glycol | 6.0 |
| (5) Fragrance | 0.08 |
| (6) Glyceryl tri2-ethylhexanoate | 2.0 |
| (7) Di-2-ethylhexyl succinate | 3.0 |
| (8) 2-Ethylhexyl p-methoxycinnamate | 5.0 |
| (9) Avobenzone | 3.0 |
| (10) Bis-ethylhexyloxyphenol methoxyphenyl triazine | 1.0 |
| (11) Quaternium-5 hectorite | 2.0 |
| (12) 1,3-Butylene glycol | 5.0 |
| (13) Phenoxyethanol | 0.5 |
| (14) Glycerin | 9.0 |
| (15) EDTA-trisodium salt | 0.1 |
| (16) Erythritol | 0.1 |
| (17) Ion exchange water | Balance |

(Production Method)

The emulsification was carried out by a routine method to obtain the sun block cream. The obtained sun block cream was not sticky but refreshing when used, and had good stability.

TABLE 14

| Example 8 W/O Cream | Content % by mass |
|---|---|
| (1) Polyoxyethylene (6 mol) behenic acid | 0.2 |
| (2) Polyoxyethylene (10 mol) behenyl ether | 0.2 |
| (3) Polyoxyethylene (10 mol) phytosterol | 0.6 |
| (4) Sorbitan sesquioleate | 0.2 |
| (5) Ion Exchange water | Balance |
| (6) Fragrance | 0.02 |
| (7) Dimethylpolysiloxane *1 | 5.4 |
| (8) Liquid paraffin | 15.0 |
| (9) Cetyl isooctanoate | 5.0 |
| (10) Purified vaseline | 10.0 |
| (11) Dipropylene glycol | 5.0 |
| (12) Microcrystalline wax | 0.5 |
| (13) Quaternium-5 hectorite | 2.2 |
| (14) Phenoxyethanol | 0.5 |
| (15) Glycerin | 7.0 |
| (16) Dipropylene glycol | 3.1 |
| (17) 1,3-Butandiol | 3.0 |
| (18) Camomile extract | 0.1 |
| (19) Citric acid | 0.02 |
| (20) Sodium citrate | 0.08 |

(Production Method)

The emulsification was carried out by a routine method to obtain the cream. The obtained cream was not sticky but refreshing when used, and had good stability.

We claim:

1. An α-gel forming composition, comprising:
    at least one polyoxyethylene derivative selected from the group consisting of polyoxyethylene dialkyl ester and polyoxyethylene dialkyl ether having a formula (I);

(I)

at least one polyoxyethylene derivative selected from the group consisting of polyoxyethylene alkyl ester and polyoxyethylene alkyl ether having a formula (II);

(II)

and at least one polyoxyethylene sterol ether having a formula (III):

(III)

wherein each R, R1 and R2 is at least one residue selected from the group consisting of a straight-chain aliphatic acid residue and a straight-chain aliphatic alcohol residue, said each straight-chain comprise 16 to 24 carbon atoms, and n in said formula (I) is an integer in a range of 4 to 15, and n in said formula (II) is an integer in the range of 8 to 30, and R3 is a cholesterol and phytosterol residue, and n in said formula (III) is an integer in a range of 5 to 30;

wherein said polyoxyethylene derivative having said formula (I) is in a range of 15 to 50% by mass, said polyoxyethylene derivative having said formula (II) is in a range of 5 to 80% by mass, and said polyoxyethylene sterol ether is at most 80% by mass, respectively based on said total amount of polyoxyethylene surfactants in said external skin care composition; and wherein upon an external combination with water, said α-gel forming composition forms an α-gel upon an evaporation of said water.

2. The α-gel forming composition according to claim 1, wherein:

said water is 10 to 55% by mass in said α-gel forming composition.

3. An external skin care composition, comprising:

said α-gel forming composition according to claim 2.

4. An external skin care water-in-oil composition, comprising:

said external skin care composition according to claim 3.

5. The external skin care water-in-oil composition, according to claim 4, comprising:

at least one selected aliphatic derivative from the group consisting of aliphatic alcohols and fatty acids.

6. An external skin care oil-in-water composition, comprising:

said external skin care composition according to claim 3.

7. An α-gel composition, comprising:

at least one polyoxyethylene derivative selected from the group consisting of polyoxyethylene dialkyl ester and polyoxyethylene dialkyl ether having a formula (I);

(I)

at least one polyoxyethylene derivative selected from the group consisting of polyoxyethylene alkyl ester and polyoxyethylene alkyl ether having a formula (II);

(II)

and at least one polyoxyethylene sterol ether having a formula (III):

(III)

wherein each R, R1 and R2 is at least one residue selected from the group consisting of a straight-chain aliphatic acid residue and a straight-chain aliphatic alcohol residue, said each straight-chain comprise 16 to 24 carbon atoms, and n in said formula (I) is an integer in a range of 4 to 15, and n in said formula (II) is an integer in the range of 8 to 30, and R3 is a cholesterol and phytosterol residue, and n in said formula (III) is an integer in a range of 5 to 30.

* * * * *